(12) United States Patent
Valencic et al.

(10) Patent No.: US 6,755,826 B2
(45) Date of Patent: Jun. 29, 2004

(54) UROLOGICAL RESECTOSCOPE HAVING AN INSULATING CASE

(75) Inventors: Maksim Valencic, Matulji (CR); Felix Nussbaum, Hamburg (DE); Thomas Wosnitza, Lüneburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 258 days.

(21) Appl. No.: 10/142,020

(22) Filed: May 9, 2002

(65) Prior Publication Data

US 2002/0193792 A1 Dec. 19, 2002

(30) Foreign Application Priority Data

May 9, 2001 (DE) .......................................... 101 22 465

(51) Int. Cl.[7] ............................................. A61B 18/18
(52) U.S. Cl. ............................................. 606/46; 604/22
(58) Field of Search .......................... 606/46, 45, 41, 606/49, 170, 180; 604/22

(56) References Cited

U.S. PATENT DOCUMENTS

| | | | | |
|---|---|---|---|---|
| 3,990,456 A | * | 11/1976 | Iglesias ........................ | 606/46 |
| 4,030,502 A | * | 6/1977 | Iglesias ........................ | 606/46 |
| 4,506,668 A | | 3/1985 | Konig | |
| 5,088,998 A | * | 2/1992 | Sakashita et al. ............. | 606/46 |
| 6,159,209 A | * | 12/2000 | Hakky .......................... | 606/45 |
| 6,491,690 B1 | * | 12/2002 | Goble et al. .................. | 606/41 |

| | | | | |
|---|---|---|---|---|
| 6,607,529 B1 | * | 8/2003 | Jones et al. ..................... | 606/47 |

FOREIGN PATENT DOCUMENTS

DE 2617556 C2 * 11/1996 ........... A61B/17/38

OTHER PUBLICATIONS

Richard Wolf GmbH catalogue, Low Pressure Cont. Irrigation Resectoscopes, D 17.
Richard Wolf GmbH catalogue, Continuous Irrigation Resectoscope, D 12.
Richard Wolf GmbH catalogue, Continuous Irrigation Resectoscope, D12.
Richard Wolf GmbH catalogue, Low Pressure Cont. Irrigation Resectoscopes, D 17.

* cited by examiner

*Primary Examiner*—Michael Peffley
*Assistant Examiner*—Peter Vrettakos
(74) *Attorney, Agent, or Firm*—Rankin, Hill, Porter & Clark LLP

(57) ABSTRACT

A urological resectoscope having an outer stem fitted with orifices at its distal terminal zone and an inner stem, both stems being tubular and metallic and being sealed from each other in the distal end zone and being affixed to each other, optionally in detachable manner, and to a main case. The resectoscope also includes an electrode support running longitudinally through the inner stem and bearing an hf-loaded cutting loop at its distal end. Liquid hookups feed liquid into the inner stem and drain liquid from an annular duct defined between the inner and outer stems. A distally affixed tubular insulating shell is disposed between the inner and outer stems and affixed to the outer stem.

11 Claims, 3 Drawing Sheets

UROLOGICAL RESECTOSCOPE HAVING AN INSULATING CASE

BACKGROUND OF THE INVENTION

The present invention relates to a urological resectoscope.

A resectoscope of a different kind is disclosed in the German patent 2,428,000 and shown in its FIG. 8. The author of this document is Dr. Iglesias who therein disclosed the first permanently rinsing resectoscope. Separate feed and drain ducts to rinse the region of the field of view are assured by the double-stem design, and as a result resecting with a clear view shall be assured for a long time.

As regards the latter resectoscopes, resecting entails first distally advancing the cutting loop and then retracting it while cutting through the tissue. In order to cut off cleanly the tissue strips, the cutting loop must cut against the distal stem rim constituting one cutting edge. The stem will be strongly heated in this process. Accordingly, the distal rim zone of the stem must consist of a high-temperature resistant material, which furthermore shall be electrically insulating in order to preclude hf contact with the surgeon holding the resectoscope.

In the design disclosed in the above reference, the shading (per US standard) denotes the outer stem that constitutes the cutting edge for the non-conducting cutting loop. However, substantial costs and handling difficulties are incurred by making the entire outer stem of plastic or ceramic.

Accordingly the German Gebrauchsmuster 7,426,959 proposed a design of the above species wherein both stems are metallic and a separate insulating shell constituting the cutting edge is used. In this design the insulating shell is affixed to the inner stem. This design has become the present-day standard. This design entails a slight drawback, which however becomes significant in medical use.

The tubular insulating shell constitutes the end element of the inner stem. Because of the required annular space between the stems, the diameter of the other stem is larger than that of the insulating shell. On the other hand the insulating shell's inside diameter determines the maximum size of the cutting loop. As a result, this design entails an outside diameter substantially larger than that of the cutting loop.

The surgeon desires the largest possible cutting loop so as to be able to slice off the biggest strips as fast as possible. On the other hand, he desires a resectoscope of minimal outside diameter in order not to unduly stretch the tissue duct through which the resectoscope is being inserted, usually the human urethra, which would entail traumatic tissue tearing. The differential of the inside insulating shell diameter and the outside outer stem diameter therefore should be minimized. However, the resectoscope of the state of the art gave rise to the above cited problems.

SUMMARY OF THE INVENTION

An objective of the present invention is to create a resectoscope of the above kind wherein the differential of the inside insulating shell diameter and the outside outer stem diameters may be reduced.

As regards the invention, and contrary to the state of the art, the insulating shell is not affixed to the inner stem but instead to the outer stem. In particular, the insulating shell may exhibit the same diameter as the outer stem. In this configuration, the inner stem may be radially sufficiently spaced from the outer stem to subtend a return flow duct of large volume. The diameter differential of the inner insulating shell stem and outer stem thereby can be reduced to the insulating shell's wall thickness. Without incurring further drawbacks, this design, when applied to otherwise conventional resectoscopes, allows reducing the outside diameter by about 1 mm, or, with the outside diameter remaining constant, the loop diameter may be enlarged by about 1 mm. Considering that to-date decades have been spent in attaining reductions of several tenths of a mm only, the invention amounts to a gigantic step forward.

Moreover, in this design, the cutting-loop diameter shall not be constrained by the inside diameter of the inner stem. The cutting loop is conventionally supported by prongs present at the distal end of the electrode support. The prongs are spaced apart as much as possible in order to reliably hold in place the cutting loop. However, to create a large-volume return flow duct, the inside diameter of the inner stem must be small. In accordance with the present invention, an inner stem subtending a small volume allows creating a large-volume return flow duct, yet the prongs running in outwardly convex grooves of the inner stem may be substantially apart from each other.

In further accordance with the present invention, the inner stem may distally project by its distal rim beyond the insulating shell and rest by its inside in sealing manner against said insulating shell. However, the inner stem also may abut the proximal insulating shell rim in order to implement thereby an especially smooth transition and in order not to restrict the free length of the insulating shell required for the cutting loop's excursion.

As regards modern resectoscopes, their two stems rest in mutually rotatable manner at their proximal affixation site in the manner shown in the German patent disclosure DE 410 1472 C2. When continuously rotating the resectoscope in order to allow cutting at different angular positions, for instance as required especially in prostate resection, the invention attains the advantage that, while the cutting loop and the inner stem are being rotated, the outer stem may rest free of rotation relative to and in the urethra and thus remain in the urethra without causing trauma to it. This feature offers the further advantage that, when using the design of the German Gebrauchsmuster 74 26959 for the distal stem zones having an insulating body mounted to the inner stem and in the form of a slanted beak, the beak shape rotates together with the cutting loop and therefore provides a constant cutting edge. The beveled beak shape provides hydrodynamic advantages.

On the other hand, if the insulating shell is firmly affixed to the outer stem and if the cutting loop is being rotated, then initially only a straight-cut, distal terminal edge of the insulating shell may be selected because it alone shall assure constant cutting conditions in all directions of rotation. However, according to a further feature o the invention, the insulating shell still is mounted on the outer stem, but in a rotatable manner relative to it, and it is linked to the inner stem to rotate with latter. When the inner stem together with the cutting loop is being rotated, the cutting loop is therefore also rotated. This design offers the advantage that the insulating shell now can be fitted with the desired beveled beak shape.

In further accordance with the present invention, if the distal inner-stem rim is configured obliquely, there will be zones of the distal edge that are distally farther and zones that are closer to the proximal end of the instrument. The annular space subtended between the inner and outer stems are more distal at the more distal zones and orifices may be provided at the more distal zones to aspirate distally far out liquid. This feature is advantageous in case the resectoscope outer stem is tightly enclosed almost to its distal end. As a result and even under unfavorable conditions, unhampered permanent rinsing may still be assured. Advantageously, the bevel of the distal inner-stem rim may be selected such that the rim is more proximal within the circumferential zone that encloses the central zone of the cutting loop, whereby at that location the cutting loop can be retracted enough, namely as far as into a zone opposite which there are already suction orifices.

BRIEF DESCRIPTION OF THE DRAWINGS

These and further features of the invention will be apparent with reference to the following description and drawings wherein.

DETAILED DESCRIPTION OF THE PREFERRED EMBODIMENTS

Figure 1:
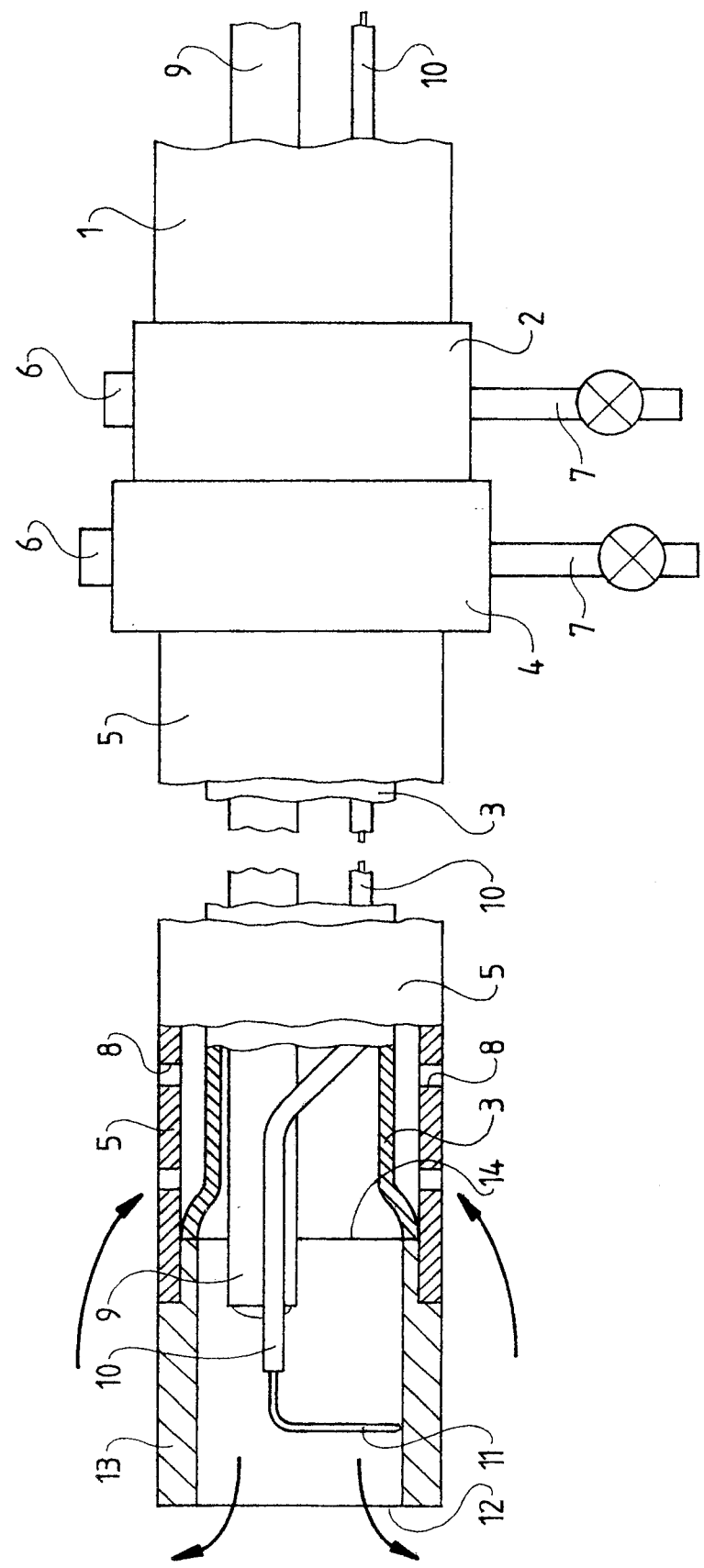
FIG. 1 is a partially cutaway side view section of the stem zone of a resectoscope of the invention.

FIG. 1 is a cutaway-section sideview of the stem of a resectoscope comprising a partly shown main case 1 from which significant elements such as the loop carriage, optics feedthrough, hf hookup etc. are omitted for the sake of clarity. These elements may be, for instance, as disclosed in the initially cited literature.

An inner stem 3 is affixed by means of a coupling 2 to the main case 1. An outer stem 5 furthermore is affixed by a coupling 4. The couplings 2, 4 can be engaged/disengaged by means of stops 6 in order to take apart the stem zone for cleaning. Rinsing hookups 7 are mounted on the couplings 2 and 4 to connect rinsing hoses to feed rinsing liquid inside the inner stem 3 and to drain it from the annular space between the inner stem 3 and the outer stem 5. As a result, the desired path of the flow takes place around the distal stem end, orifices 8 in the outer stem 5 permitting the return flow to move into the annular space. Both stems 3, 5 are conventionally made in the form of metal tubes.

Beginning at the main case 1, an optics 9 runs inside the inner stem 3 and is mounted in a conventionally exchangeable manner. An electrode support 10, which is designed, for instance, in the manner of FIG. 10 of the initially cited reference, is mounted in a longitudinally displaceable manner inside the inner stem 3 and supports a cutting loop 11 at its tip.

An hf current is applied to the cutting loop 11, which in surgery shall be pulled back against the stem's cutting edge 12. Therefore, the distal end zone is made of a high-temperature resistant and insulating tubular insulating shell 13.

As shown in FIG. 1, the insulating shell 13 is firmly joined, by surface-to-surface bonding or the like, with the outer stem 5. The inner stem 3 is detachable from the outer stem 5 and, hence, from the insulating shell 13 and it flares at its distal end zone, and, as shown in FIG. 1, abuts the proximal rim 14 of the insulating shell 13.

Figure 2:
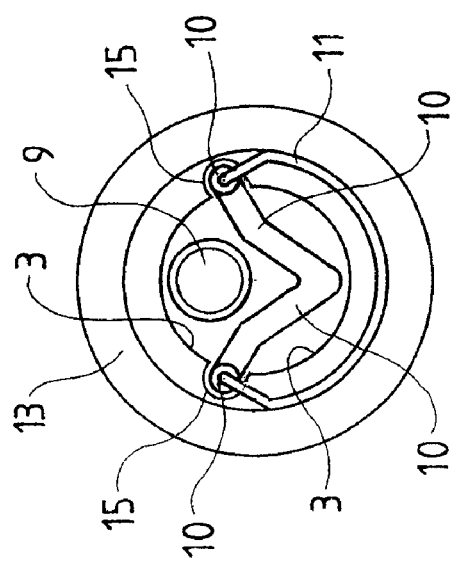
FIG. 2 is a distal axial section of the of the resectoscope of FIG. 1.

As shown in FIG. 2, the cutting loop 11 runs tightly against a portion of the inside circumference of the insulating shell 13 in order to cut off tissue of the largest possible diameter. In the distal end zone, the electrode support 10 subtends the two prongs shown in FIG. 2, which for improved dimensional stability of the cutting loop 11 shall be spaced apart as much as possible. For that purpose the inner stem 3 is fitted with the grooves 15 shown in FIG. 2 allowing a large spacing between the prongs of the electrode support 13 provided that the annular duct between the inner and outer stems 3 and 5 subtend a large volume.

Modern design as concerns the shown embodiment configures the inner and outer stems 3 and 5 in a mutually rotatably supported manner by commensurately specifying the couplings 2 and 4. Details of such a design are disclosed in the German patent document DE 410 1472 C2. When rotating the stems 3 and 5 relative to each other in the embodiment of FIG. 1, the outer stem 5 shall rotate relative to the inner stem 3, the latter being conventionally stationary relative to the main case 1 and, therefore, also being irrotational or rotationarily stationary relative to the electrode support 10 and the cutting loop 11. Therefore, the cutting loop 11 rotates relative to the insulator 13 affixed to the outer stem 5. In order to assure a constant cutting edge 12 relative to the insulating shell 13 at all angular positions of the cutting loop 11, the insulating shell 13 in the embodiment illustrated in FIG. 1 is cut off straight at its distal end.

Figure 3:
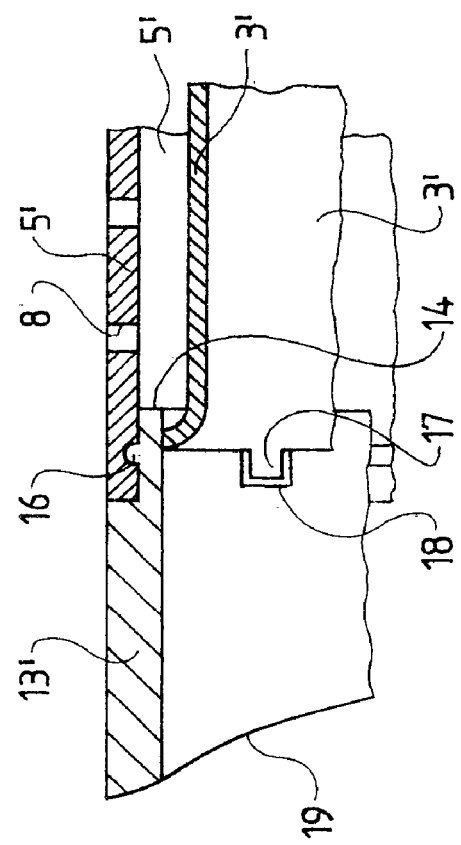
FIG. 3 is a distal cutaway of FIG. 1 of an embodiment variation comprising a rotatable insulating shell.

FIG. 3 shows an embodiment variation of FIG. 1 and elucidates only the modified parts that are primed over the references shown in FIGS. 1 and 2. The remaining parts correspond to the embodiment of FIGS. 1 and 2.

In this design variation the insulator 13' again is affixed to the outer stem 5', however not in a stationary manner, but rather in a rotary manner relative to the stem. FIG. 3 shows the flange in the form of a sliding bearing fitted with a groove-and-spring engagement 16 to assure rotatable affixation secured against disengagement.

FIG. 3 shows a rotational coupling between the inner stem 3' and the insulating shell 13'. The rotary coupling is schematically shown as a protrusion 17' at the distal rim of the inner stem 3', the protrusion entering a clearance 18 in the insulating shell 13'. Other rotational coupling designs also are applicable.

In the embodiment of FIG. 3, rotation of the outer stem 5' relative to the inner stem 3' entails rotating the insulating shell 13' together with the inner stem 3', that is, also together with the main case 1 and the cutting loop 11. Therefore, the cutting loop always shall be irrotational or non-rotatable relative to the insulating shell 13', which on that account and as shown may assume the known beak shape with beveled distal rim 19.

This inner stem 3' may be designed in the manner shown in FIG. 1 and in the embodiment of FIG. 3 it may rest against the proximal edge 14 of the insulating shell 13'. In one embodiment variation, however, said stem 3' is designed to rest by its flaring distal rim against the inside surface.

If, in a design modified from the one above, the distal rim of the inner stem 3' were to be distally farther out, that is, if it were to overlap the insulating shell 13' more, then additional but omitted orifices may be fitted into the insulating shell 13' to assure improved return flow to the annular duct between the inner and outer stems 3' and 5', respectively.

If in the most typical application a resectoscope is placed through the urethra as far as into the prostate zone in order to cut by means of the cutting loop in that region, then the full length of the outer stem as far as into immediate distal end region shall be firmly enclosed by the urethra. In that case, the orifices 8 in the outer stem shall be closed.

Accordingly, care must be taken that these orifices shall be configured as far distally as possible. This objective may be attained by using another design variation shown in FIG. 4. Again, and to the extent, possible identical parts are denoted by identical references or are supplemented by double primes.

Contrary to the case of the embodiments of FIGS. 1 through 3, the distal rim 20 of the inner stem 3" is beveled in this embodiment. The distal rim 20 is situated in FIG. 4 distally farther away at the top than at the bottom. The most advanced orifice 8" at the top therefore is configured distally farther than would be possible in the embodiments of FIGS. 1 through 3 wherein the inner stem rim is straight. As a result, even when the outer stem is enclosed very far distally, this orifice 8" will still assure permanent rinsing.

Figure 4:
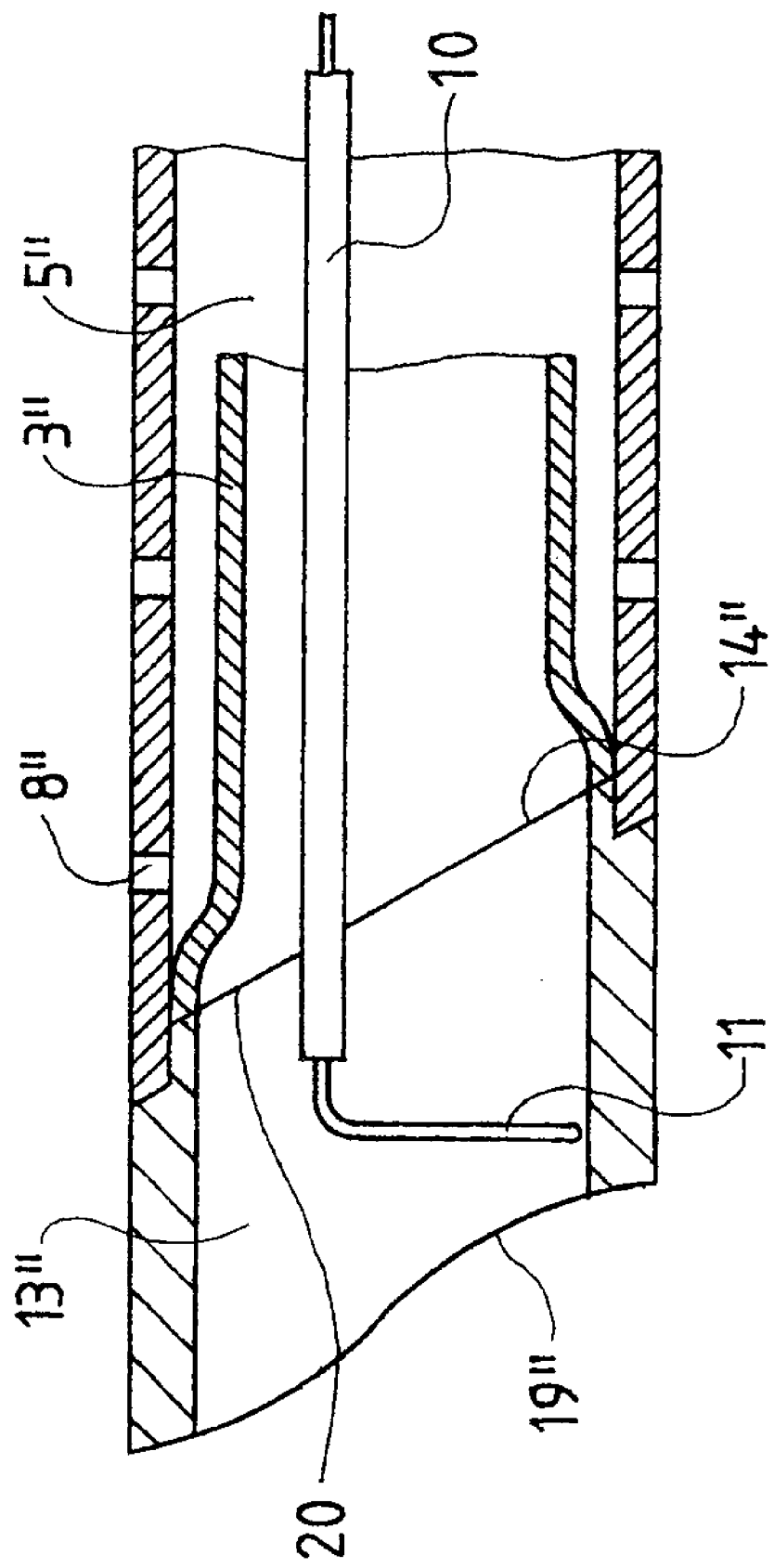
FIG. 4 is a view similar to FIG. 3 of an embodiment variation comprising a distally beveled inner stem.

In its other aspects, the embodiment of FIG. 4 corresponds to the embodiment details of FIG. 1 except that the distal rim 19" of the insulating shell 13" is beveled like a beak as in the embodiment of FIG. 3. The beveled rims 20 and 19" run substantially parallel. The bevel is selected such that the distal rim 20 of the inner stem 3" is proximally farther out in the region where the cutting loop 11 touches the insulating shell 13". Accordingly, while resting against the insulating shell 13", the cutting loop 11 can be retracted in the proximal direction far enough that it will already be situated at the level of the most advanced orifice 8".

As shown by FIG. 4, this design is selected to correspond to that of FIG. 1 such that the distal rim 20 of the inner stem 3" rests against the proximal edge 14" of the insulating shell 13". However, on account of the beveled design of FIG. 4, the distal rim of the inner stem 3" also may be designed as shown in FIG. 3 so that it will abut the inside wall of the insulating shell 13'. In that case, the distal rim of the inner stem 3" may be shifted even somewhat farther distally and the most advanced orifice 8"—which in the embodiment of FIG. 4 traverses the outer stem 5"—may now be mounted to traverse the insulating shell 13".

Further but omitted embodiment variations are possible. As already mentioned in relation to FIG. 1, the outer and inner stems 5 and 3 may be detachably affixed to the main case 1. As was mentioned already with respect to FIG. 3, the inner stem 3' and the cutting loop 11 may be mutually irrotational whereas the outer stem 5' is rotatable relative to both.

In a further embodiment mode the inner stem may be firmly affixed on the main case 1 and only the outer stem may be detachable and, where called for, it may be rotatably supported.

In another but not illustrated embodiment variation both stems, that is the outer stem as well as the inner stem, may be irrotationally affixed to the main case 1, where called for in detachable manner, whereas the cutting loop 11 rests in rotatable manner on the main case 1 on account of an appropriate rotatable configuration of the loop carriage.

What is claimed is:

1. A urological resectoscope comprising an outer stem (5, 5') and an inner stem (3, 3'), said inner and outer stems having a proximal terminal zone and a distal terminal zone, said outer stem distal terminal zone fitted with orifices (8), wherein said inner and outer stems are tubular and metallic and are sealed from each other at said distal terminal zones and are mutually affixed to one another in a detachable manner at said proximal terminal zones, said outer and inner stems are mounted on a main case (1), said resectoscope further comprising an electrode support (10) traversing said inner stem and mounted in a longitudinally displaceable manner within said inner stem, said electrode support supporting an hf loaded cutting loop (11), and further comprising liquid hookups (7) to feed liquid into the inner stem and to drain liquid from an annular space between the inner and outer stems, and a distally affixed, tubular insulating shell (13, 13'), wherein the insulating shell (13') is rotatably affixed to the outer stem (5') and is linked (17, 18) with the inner stem (3') so as to jointly rotate with said inner stem.

2. The resectoscope as claimed in claim 1, wherein an outside diameter of the insulating shell (13, 13') is identical to an outside diameter of the distal end zone of the outer stem (5, 5').

3. The resectoscope as claimed in claim 1, wherein the cutting loop (11), when in a proximal end position, is configured distally from the distal end of the inner stem (3, 3').

4. The resectoscope as claimed in claim 1, wherein the inner stem (3, 3') is fitted with longitudinal grooves (15) to receive prongs of the electrode support (10) that bear the cutting loop (11).

5. The resectoscope as claimed in claim 1, wherein an inside diameter of the insulating shell (13) is smaller than an inside diameter of the outer stem (5) and wherein the inner stem (3) rests, via a diametrically enlarged distal rim, against a proximal edge of the insulating shell (14).

6. The resectoscope as claimed in claim 1, wherein a distal rim (20) of the inner stem (3") runs obliquely to the stem axis.

7. A urological resectoscope comprising an outer stem (5, 5') and an inner stem (3, 3'), said inner and outer stems having a proximal terminal zone and a distal terminal zone, said outer stem distal terminal zone fitted with orifices (8), wherein said inner and outer stems are tubular and metallic and are sealed from each other at said distal terminal zones and are mutually affixed to one another in a detachable manner at said proximal terminal zones, said outer and inner stems are mounted on a main case (1), said resectoscope further comprising an electrode support (10) traversing said inner stem and mounted in a longitudinally displaceable manner within said inner stem, said electrode support supporting an hf loaded cutting loop (11), and further comprising liquid hookups (7) to feed liquid into the inner stem and to drain liquid from an annular space between the inner and outer stems, and a distally affixed, tubular insulating shell (13, 13'), wherein the insulating shell (13, 13') is affixed to the outer stem (5, 5') and wherein an inside diameter of the insulating shell (13) is smaller than an inside diameter of the outer stem (5) and wherein the inner stem (3) rests, via a diametrically enlarged distal rim, against a proximal edge of the insulating shell (14).

8. The resectoscope as claimed in claim 7, wherein an outside diameter of the insulating shell (13, 13') is identical to an outside diameter of the distal end zone of the outer stem (5, 5').

9. The resectoscope as claimed in claim 7, wherein the cutting loop (11), when in a proximal end position, is configured distally from the distal end of the inner stem (3, 3').

10. The resectoscope as claimed in claim 7, wherein the inner stem (3, 3') is fitted with longitudinal grooves (15) to receive prongs of the electrode support (10) that bear the cutting loop (11).

11. The resectoscope as claimed in claim 7, wherein a distal rim (20) of the inner stem (3") runs obliquely to the stem axis.

* * * * *